United States Patent [19]

Fréhel et al.

[11] Patent Number: 4,523,013
[45] Date of Patent: Jun. 11, 1985

[54] 4-ACYL-2,6-DIOXO-1-PHENETHYL PIPEROZINES

[75] Inventors: Daniel Fréhel, Toulouse; Jean-Pierre Maffrand, Portet-sur-Garonne, both of France

[73] Assignee: Sanofi, S.A., Toulouse, France

[21] Appl. No.: 462,397

[22] Filed: Jan. 31, 1983

[30] Foreign Application Priority Data

Jan. 29, 1982 [FR] France ................. 82 01758

[51] Int. Cl.$^3$ ............................. C07D 241/08
[52] U.S. Cl. ..................... 544/385; 544/344; 544/382; 544/384; 546/139; 546/145; 546/146; 546/147
[58] Field of Search ......................... 544/385

[56] References Cited

U.S. PATENT DOCUMENTS

| | | | |
|---|---|---|---|
| 3,171,837 | 3/1965 | Freed | 544/385 |
| 3,239,582 | 3/1966 | von Bebenburg et al. | 544/385 |
| 3,969,316 | 7/1976 | Ramey et al. | 544/385 |

FOREIGN PATENT DOCUMENTS

| | | |
|---|---|---|
| 624686 | 3/1963 | Belgium . |
| 1795728 | 3/1974 | Fed. Rep. of Germany . |
| 2362539 | 8/1975 | Fed. Rep. of Germany . |
| 2441261 | 3/1976 | Fed. Rep. of Germany . |
| 2504250 | 8/1976 | Fed. Rep. of Germany . |
| 943M | 2/1961 | France ........................ 544/385 |
| 966802 | 8/1964 | United Kingdom ........... 544/385 |

OTHER PUBLICATIONS

Irikura, "Chemical Abstracts", vol. 84, 1976, Col. 180288r; 180889s.

Primary Examiner—Glennon H. Hollrah
Assistant Examiner—James H. Turnipseed
Attorney, Agent, or Firm—Weiser & Stapler

[57] ABSTRACT

2-Acyl-1,3,4,6,7,11b-hexahydro-2H-pyrazino-[2,1-a]-4-isoquinoleinones having anthelmintic activity of the formula

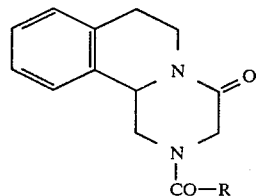

are prepared from 4-acyl-2,6-dioxopierazines by reaction with a phenethyl halide, selective reduction of one of the oxo groups and cyclization, by the novel intermediates of formula

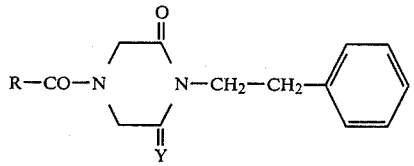

in which Y represents O or H, OH.

6 Claims, No Drawings

4-ACYL-2,6-DIOXO-1-PHENETHYL PIPEROZINES

The present invention relates to a process for the preparation of 2-acyl-1,3,4,6,7,11b-hexahydro-2H-pyrazino-[2,1-a]-4-isoquinoleinones.

The present invention has more particularly for its object a novel process for the preparation of compounds of formula

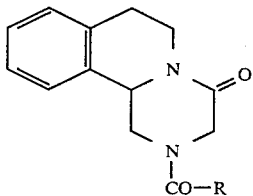

I in which R represents a lower alkyl group, cycloalkyl having 3 to 8 carbon atoms, phenyl or substituted phenyl.

The 2-acyl-1,3,4,6,7,11-b-hexahydro-2H-pyrazino-[2,1-a]-4-isoquinoleinones of formula I as indicated above are products which are well known and which are described in German Pat. Nos. 1 795 728 and 2 362 539, as powerful anthelmintics or as intermediaries in the preparation of products having anthelmintic activity.

The foregoing compound of formula I, in which R is a cyclohexyl group, has been given the Common International Denomination of "praziquantel" and it has been indicated as having a broad anthelmintic spectrum with an excellent activity with respect to all of the pathogenic species of Schistosomes in human beings and the Cestodes (Experientia).

The German Pat. Nos. 2 362 539 and 2 441 261 describe a process which can be used for the preparation of the compounds of the general formula I as indicated above, the said process being characterised in that 4-oxo-1,2,3,6,7,11b-hexahydro-2H-pyrazino-[2,1-a]-isoquinoleine of formula

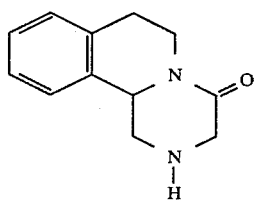

II is treated with the R—COOH acid, or with one of its functional derivatives, or even that a compound of formula

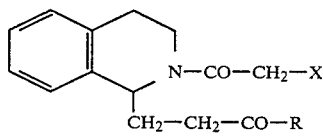

III in which X represents a halogen, a methylsulphonyloxy group or an arylsulphonyloxy group containing 6 to 10 carbon atoms, is treated in the presence of a cyclising agent, or even, when it is a question of preparing diastereoisomers, a compound of formula

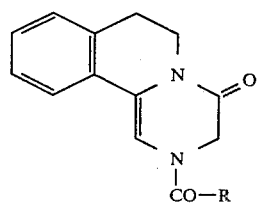

IV in which the dotted line indicates that it may have a double bond in the 6,7-position, is treated with a reduction agent.

According to German Pat. No. 2 504 250, the starting product III has the disadvantage that it is only available with very small yields from the isoquinoleine, the acid chloride R—COCl and the cyanides.

The same patent discloses a process which is characterised in that a compound of formula

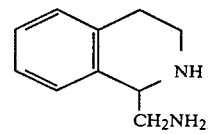

V in the form of addition mono-salts, is treated with the R—COCl chloride in the presence of a weak base, which is slightly more basic than the product which is obtained, and then the compound as obtained is transformed into the compound III as indicated above by the action of a halogenoacetyl halide.

The compounds III are then transformed into the compounds of the aforementioned formula I in accordance with the process of German Pat. No. 2 362 539.

The compound of formula V is, in its turn, prepared by catalytic hydrogenation of the compound of formula

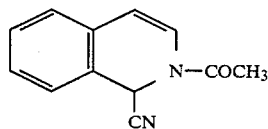

VI preferably by using Raney nickel as catalyst [Helv. Chim. Acta. 1939, 22, 673–683], and then by hydrolysis. However, already for quantities of from 150 to 200 mg, this hydrogenation comprises an operation at a high temperature and at a very high pressure (of at least 150 to 250 atmospheres), this representing a disadvantage at industrial level, particularly when the quantities are even greater.

The German Pat. No. 2 457 971 describes another process for the preparation of compounds of the aforementioned formula I, which consists in the cyclisation of a compound of formula

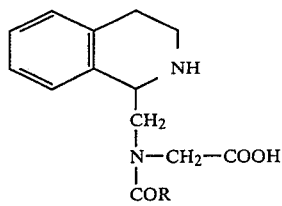

or one of its functional derivatives on carboxyl.

However, the compounds VII are prepared from the aforementioned product V, for which high temperatures and pressures are necessary for the obtaining thereof.

According to the same patent, it is also possible to cyclise a compound of formula

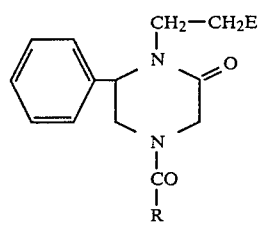

in which E is a halogen or a hydroxyl group, but this procedure is not that which is preferred by comparison with that which comprises the cyclisation of the product VII.

Under all circumstances, all the methods which lead to the products of formula I with suitable yields comprise primarily either a hydrogenation at very high pressures and temperatures, in the presence of catalysts such as Raney nickel, which necessitate careful preparation, or other processes which comprise, for example, the use of hydrofluoric gas or of expensive intermediate containing silicon.

It has now been found that the compounds of the aforementioned general formula I can be prepared with high total yields by the process according to the present invention, which makes use of novel intermediaries and of chemical reactions which can be easily carried into effect and of which the transfer to an industrial scale is simple.

Thus, according to one of its features, the present invention is concerned with a process for the preparation of 2-acyl-1,3,4,6,7,11b-hexahydro-2H-pyrazino-[2,1-a]-4-isoquinoleinones of formula I as indicated above, the said process being characterised in that a 4-acyl-2,6-dioxopiperazine of formula

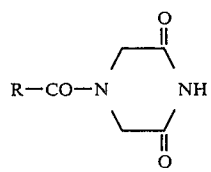

is treated with an alkylating agent of formula

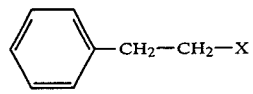

in which X represents chlorine, bromine, iodine or a nucleophobic group, in the presence of an alkaline condensation agent in an inert organic solvent; one of the imidic carbonyls of the compound as thus obtained and of formula

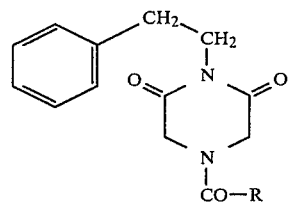

is reduced by a complex metal hydride in the presence of a metallic chloride catalyst which is selected from $CuCl_2$, $CoCl_2$, $NiCl_2$, $CrCl_3$, $FeCl_3$, $SnCl_2$, $SrCl_2$, $MnCl_2$, $CeCl_2$, $HgCl_2$, and the compound thus obtained and of formula

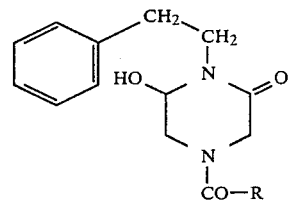

is cyclised by action of a strong organic or mineral acid at a temperature which is between 0° and 25° C.

According to another of its features, the present invention has for its object to provide, as intermediates, novel 4-acyl-6-oxo-1-phenethyl piperazines of formula

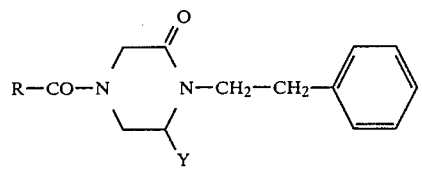

in which R is as defined above and in which Y is O or H,OH.

The steric configuration of the hydroxyl in the 2-position of the compounds XII as indicated above is of no significance in the process of the present invention, because the cyclisation passes through a carbonation which destroys the asymmetric centre in the 2-position and the final products are obtained with a practically quantitative yield.

The term "lower alkyl" as used herein, designates a straight-chain or branched-chain saturated aliphatic hydrocarbon radical which contains up to 6 carbon atoms, such as methyl, ethyl, propyl, isopropyl, isobutyl, sec.-butyl, tert.-butyl and similar radicals.

The term "substituted phenyl", as used herein, designates a phenyl group which is monosubstituted or disubstituted by an atom or a radical which is inert under the above reaction conditions, for example, a halogen, such as fluorine, chlorine or bromine, a hydroxy group which is free or etherified with a lower alkyl such as defined above, an amino group which is free or monosubstituted or disubstituted by a lower alkyl, such as defined above, a mercapto group which is free or thioetherified with a lower alkyl group, such as defined above, a cyano group, a trifluomethoxy group or trifluomethylthio group.

The reaction between the initial compound of formula IX as indicated above and the reagent of formula X is an alkylation conducted in the presence of an alkali condensation agent, such as sodium hydride, an alkali alcoholate and similar agents. The nucleophobic group indicated by X in the aforementioned formula X is preferably the methane-sulphonyloxy (mesyloxy) group or the p-toluosulphonyloxy (tosyloxy) group, but the benzene-sulphonyloxy, β-naphthalene-sulphonyloxy and similar groups may also be used. The alkylating agents which are particularly preferred are phenethyl bromide and phenethyl iodide.

According to one preferred operational procedure, the reaction mixture is heated for 2 to 8 hours at a temperature which is between 50° and 100° C. in an inert organic solvent, such as dimethylformamide, dioxane or dimethoxyethane. On completion of the reaction, the product as thus obtained is isolated in accordance with the conventional procedure and it may be purified or used directly for the following stage.

The 4-acyl-2,6-dioxo-1-phenethyl piperazine of formula XI is then reduced with a complex metal hydride, such as the double hydride of an alkali metal or of an earth metal, such as sodium borohydride, lithium borohydride or the hydride of lithium and aluminium or even of other complex metallic hydrides, such as the borohydride of potassium and of tri-sec.-butyl in the presence of metallic chloride catalyst. The operation is generally carried out in an inert solvent such as an ether, for example, diethylether, tetrahydrofuran, dioxane or dimethoxyethane, at a temperature which is between −70° C. and the boiling point of the solvent which is used. If sodium borohydride is used, the reaction can be conducted in aqueous or hydroalcoholic solution at a temperature which is close to ambient temperature.

In accordance with a preferred working method, the operation is carried out with an excess of sodium borohydride in an alcoholic solvent, such as methanol or ethanol, at a temperature which is between 0° and 25° C., using cupric chloride ($CuCl_2$) as catalyst. After having destroyed the excess of reducing agent, the compound as thus obtained, which is 4-acyl-2-hydroxy-6-oxo-1-phenethyl piperazine of formula XII, is isolated by the conventional methods and purified or is even used as such for the cyclisation.

The cyclisation is carried out by treatment with a strong organic or mineral acid, such as hydrochloric acid, sulphuric acid, phosphoric acid, trifluoacetic acid and the like, for optimum yields at a temperature which is not above ambient, as between 0° and about 25° C. and preferably is between 0° and about 5° C. The final product of the above formula I is isolated by the reaction mixture being poured into iced water or by extraction with an appropriate solvent.

The 4-acyl-2,6-dioxopiperazines of formula IX as used as starting materials in the process of the present invention are products which are known in the literature or which are easily prepared from iminodiacetonitrile by reaction with an acid halide, by subsequent treatment of the N-acyl-iminodiacetonitrile as thus obtained with hydroxylamine and diazotisation in accordance with the following diagram

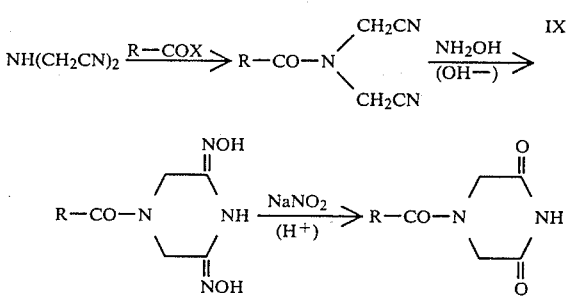

which is described in J. Chem. Soc. Perkins I, 1972, 1009.

The 4-acyl-2,6-dioxopiperazines of formula IX, as used as starting compounds, may also be prepared by causing the reaction of an N-acyl-iminodiacetic acid or the corresponding diamide with formamide, while eliminating the water which is formed azeotropically in accordance with the following diagram

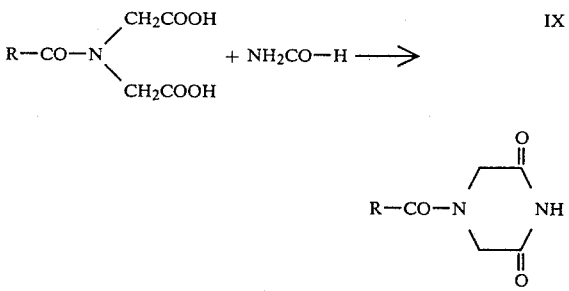

as described in Belgian Pat. No. 624 686.

The following examples illustrate the invention, without however limiting it.

PREPARATION (a) N-(cyclohexylcarbonyl)-iminodiacetonitrile

While stirring vigorously, 50 g (0.52 mol) of iminodiacetonitrile, 160 g (0.78 mol) of potassium carbonate, 150 ml of water and 400 ml of dichloromethane are mixed. After having cooled the reaction medium to 0° C., 96.5 g (0.65 mol) of cyclohexylcarbonyl chloride are added dropwise. The temperature is allowed to return to ambient temperature, while maintaining the stirring, during 2 hours. The organic phase is decanted and the aqueous phase is extracted twice with dichloromethane. The combined organic phases, dried over sodium sulphate, leave an oily residue after evaporation. By trituration with cyclohexane, crystals are recovered, and these are recrystallised from cyclohexane. White crystals, m.p.=82° C., yield: 85%.

(b) 4-(cyclohexylcarbonyl)-2,6-bis-(hydroxyimino)-piperazine

To a mixture of 19.4 g (0.28 mol) of hydroxylamine hydrochloride and 7.42 g (0.07 mol) of potassium carbonate in 60 ml of methanol and 20 ml of water are added in portions 14.4 g (0.07 mol) of N-(cyclohexylcarbonyl)-iminodiacetonitrile. The mixture is refluxed in an inert atmosphere for 2½ hours. After cooling, the crystals are filtered. These crystals are suspended in a mixture of 120 ml of ethanol and 50 ml of water and refluxed for 1 hour. The crystals are filtered while hot and these are recrystallised from a mixture of water and ethanol. White crystals, m.p.>260° C., yield: 84%.

(c) 4-(cyclohexylcarbonyl)-2,6-dioxopiperazine 6 g (0.023 mol) of 4-(cyclohexylcarbonyl)-2,6-bis-(hydroxylimino)-piperazine are suspended in a mixture of 20 ml of water and 20 ml of acetic acid. After cooling the reaction medium between 0° and 5° C., a solution of 5 g (0.069 mol) of sodium nitrite in 25 ml of water is added dropwise in an inert atmosphere. The mixture is left for 24 hours at ambient temperature. Evaporation to dryness leaves a residue, which is purified by filtration on a silica bed (elutrient: dichloromethane/methanol 9/1). The crystals which are obtained are recrystallised from ethanol. White crystals, m.p.=180° C., yield: 83%.

In the same manner, by causing the reaction of iminodiacetonitrile with cyclopropylcarbonyl chloride, cyclobutylcarbonyl chloride, cyclopentylcarbonyl chloride, cycloheptylcarbonyl chloride and respectively cyclooctylcarbonyl chloride, by treating the products thus obtained with hydroxylamine hydrochloride and by subjecting the dioximes to a diazotisation in accordance with the working procedure as described above, there are obtained 4-(cyclopropylcarbonyl)-2,6-dioxopiperazine, 4-(cyclobutylcarbonyl)-2,6-dioxopiperazine, 4-(cyclopentylcarbonyl)-2,6-dioxopiperazine, 4-(cycloheptylcarbonyl)-2,6-dioxopiperazine and, respectively, 4-(cyclooctylcarbonyl)-2,6-dioxopiperazine.

EXAMPLE 1

(a) 4-cyclohexylcarbonyl)-2,6-dioxo-1-phenethyl piperazine 15 g (0.067 mol) of 4-(cyclohexylcarbonyl)-2,6-dioxopiperazine are dissolved in 200 ml of dimethylformamide. 4 g (0.073 mol) of sodium methylate are added and the solution is left for 1 hour at ambient temperature. The reaction medium has added thereto, dropwise, in an inert atmosphere, a solution of 19 g (0.081 mol) of (2-iodoethyl)-benzene in 50 ml of dimethylformamide and it is brought to 80° C. during 5 hours. The reaction medium is evaporated to dryness, under vacuum, and the residue is taken up by a mixture of water and dichloromethane. The decanted organic phase is dried over dry sodium sulphate. The evaporation of the solvent leaves an oily residue which is purified by chromatography on a silica column (elutrient: toluene/ethyl acetate 7/3). The crystals as obtained are recrystallised from cyclohexane. White crystals, m.p.=90° C., yield: 86%.

(b) 4-(cyclohexylcarbonyl)-2-hydroxy-6-oxo-1-phenethyl piperazine 15.2 g (0.046 mol) of 4-(cyclohexylcarbonyl)-2,6-dioxo-1-phenethyl piperazine are dissolved in 600 ml of ethanol. In an inert atmosphere, at 0° C., there are added 8.7 g (0.0509 mol) of dihydrated cupric chloride and the mixture is left for 1 hour at 0° C. To the reaction medium, kept at 0° C., are added in portions 8.8 g (0.23 mol) of sodium borohydride and left for 45 minutes at 0° C. The excess of reducing agent is destroyed by adding acetone. The insoluble salts are filtered and the filtrate is evaporated to dryness. The residue obtained is treated with a mixture of water and dichloromethane. The organic phase is decanted, dried over dry sodium sulphate and evaporated to dryness. The residue which is obtained is purified by filtration on a silica bed (elutrient: ethyl acetate). Beige crystals, m.p.=134° C., yield: 73%.

(c) 2-(cyclohexylcarbonyl)-1,3,4,6,7,11b-hexahydro-2H-pyrazino-(2,1-a)-4-isoquinoleinone (PRAZIQUANTEL)

12.25 g (0.037 mol) of 4-(cyclohexylcarbonyl)-2-hydroxy-6-oxo-1-phenethyl piperazine are added in portions to 12N-hydrochloric acid, previously cooled to 0° C., and left overnight at ambient temperature. The reaction mixture is poured into iced water and extracted with dichloromethane. The organic phase, dried over dry sodium sulphate and evaporated to dryness, leaves an oil which crystallises slowly at rest. The praziquantel crystals are thus obtained are recrystallised from a mixture of petroleum ether and acetone. White crystals. M.p.=138°-140° C., yield: 95%. The total yield of praziquantel, starting from iminodiacetonitrile, starting compound of the PREPARATION, is 35%.

EXAMPLE 2

0.067 mol of 4-(cyclopropylcarbonyl)-2,6-dioxopiperazine are dissolved in 200 ml of dimethylacetamide. 0.073 mol of sodium methylate are added and the mixture is left for 1 hour at ambient temperature. To the reaction medium is added, dropwise and in an inert atmosphere, a solution of 0.081 mol of (2-ethyl tosyloxy)-benzene in 50 mol of dimethylacetamide and the mixture is brought to 90° C. for 4 hours. It is evaporated to dryness under reduced pressure, the residue is taken up in a mixture of water and methylene chloride and the decanted organic phase is dried over dry sodium sulphate. The solvent is evaporated and the residue, formed by crude 4-(cyclopropylcarbonyl)-2,6-dioxo-1-phenethyl piperazine, is dissolved in 600 ml of ethanol. The solution as thus obtained has added thereto, at 0° C. and in an inert atmosphere, 0.059 mol of manganese chloride and is left for 1 hour at 0° C. 0.23 mol of sodium borohydride is added in portions to the reaction medium, kept at 0° C., and the reaction medium is left for 45 minutes at 0° C. The excess of reducing agent is destroyed by adding acetone. The insoluble salts are filtered, the filtrate is evaporated to dryness and the residue is treated with a mixture of water and methylene chloride. The decanted organic phase is dried over dry sodium sulphate and evaporated to dryness. The residue is purified by filtration on a silica bed and the product as thus obtained, formed by the 4-(cyclopropylcarbonyl)-2-hydroxy-6-oxo-1-phenethyl piperazine, is added in portions to 150 ml of hydrochloric acid previously cooled to 0° C. After one night at ambient temperature, the reaction medium is poured into iced water and extracted with dichloromethane. The organic phase is dried on an anhydrous sodium sulphate and it is evaporated. In this way, there is obtained the 2-(cyclopropylcarbonyl)-1,3,4,6,7,11b-hexahydro-2H-pyrazino(2,1-a)-4-isoquinoleinone; m.p.=148°-149° C., yield: 57%.

In similar manner, from the 4-(cyclobutylcarbonyl)-2,6-dioxopiperazine, the 4-(cyclopentylcarbonyl)-2,6-dioxopiperazine, the 4-(cycloheptylcarbonyl)-2,6-dioxopiperazine and respectively the 4-(cyclooctylcarbonyl)-2,6-dioxopiperazine, there are obtained the (2-cyclobutylcarbonyl)-1,3,4,6,7,11b-hexahydro-2H-pyrazino-[2,1-a]-4-isoquinoleinone; m.p. 153°–156° C.; yield 55%;

the 2-(cyclopentylcarbonyl)-1,3,4,6,7,11b-hexahydro-2H-pyrazino-[2,1-a]-4-isoquinoleinone; m.p.=127°–128° C.; yield 60%;

the 2-(cycloheptylcarbonyl)-1,3,4,6,7,11b-hexahydro-2H-pyrazino-[2,1-a]-4-isoquinoleinone; m.p.=88°–91° C.; yield 57%; and respectively the 2-(cyclooctylcarbonyl)-1,3,4,6,7,11b-hexahydro-2H-pyrazino-[2,1-a]-4-isoquinoleinone; m.p.=107°–108° C.; yield 55%.

EXAMPLE 3

7.8 g (0.050 mol) of 4-acetyl-2,6-dioxopiperazine are dissolved in 200 ml of dimethoxyethane. 3.2 g (0.060 mol) of sodium methylate are added and the mixture left for 1 hour at ambient temperature.

To the reaction medium is added, dropwise and in an inert atmosphere, a solution of 13 g (0.070 mol) of (2-bromoethyl)-benzene in 50 ml of dimethoxyethane and this is brought to 85° C. in 5 hours. It is evaporated to dryness, under vacuum, and the residue is taken up by a mixture of water and dichloromethane. The decanted organic phase is dried over dry sodium sulphate. The oily residue which is obtained is purified by chromatography on a silica column (elutrient: toluene/ethyl acetate 7/3). In this way, there is obtained the 4-acetyl-2,6-dioxo-1-phenethyl piperazine which, after recrystallisation from a mixture of ethyl acetate/isopropanol, melts at 130° C.

The product thus obtained is dissolved in 500 ml of ethanol. 7.15 g (0.055 mol) of $CcCl_2$ are added at 0° C. in an inert atmosphere and the mixture is left for 1 hour at this temperature. The reaction medium has added thereto, in portions and at 0° C., 9.5 g (0.25 mol) of sodium borohydride and is left for 45 minutes at 0° C. The excess of reducing agent is destroyed by acetone, the insoluble salts are filtered and the filtrate is evaporated to dryness. The residue obtained is treated with a mixture of water and dichloromethane. The organic phase is decanted, then dried over dry sodium sulphate and evaporated to dryness. The residue which is obtained is purified by filtration on a silica bed (elutrient: ethyl acetate), the product as thus obtained is added in portions to 150 ml of 12N-hydrochloric acid, previously cooled to 0° C., and left overnight at ambient temperature. The reaction medium is poured into iced water and extraction is carried out with dichloromethane. The organic phase is dried over dry sodium sulphate and evaporated to dryness. In this way, there is obtained the 2-acetyl-1,3,4,6,7,11b-hexahydro-2H-pyrazino-[2,1-a]-4-isoquinoleinone, and this, after recrystallisation from a mixture of petroleum ether and acetone, melts at 140°–141° C. Total yield: 60%.

EXAMPLE 4

12 g (0.055 mol) of 4-benzoyl-2,6-dioxopiperazine are dissolved in 200 ml of dimethylformamide. 3.5 g (0.065 mol) of sodium methylate are added and the reaction medium is left for 1 hour at ambient temperature. To the reaction medium is added, dropwise and in an inert atmosphere, a solution of 16 g (0.080 mol) of (2-methane-sulphonyl ethyl)-benzene in 50 ml of dimethylformamide and is brought to 70° C. for 5 hours. Evaporation to dryness is carried out under vacuum and the residue is taken up in a mixture of water and dichloromethane. The decanted organic phase is dried over dry sodium sulphate. The evaporation of the solvent leaves an oily residue which is purified by silica column chromatography (elutrient: toluene/ethyl acetate 7/3). In this way, there is obtained the 4-benzoyl-2,6dioxo-1-phenethyl piperazine which, after recrystallisation from a cyclohexane/ethyl acetate mixture, melts at 102° C.

16.1 g (0.050 mol) of the product as thus obtained are dissolved in 600 ml of ethanol. In an inert atmosphere, at 0° C., there are added 8.94 g (0.055 mol) of ferric chloride and the medium is left for 1 hour at 0° C. To the reaction medium, kept at 0° C., are added in small quantities 9.5 g (0.25 mol) of sodium borohydride and the medium is left for 1 hour at 0° C. The excess of reducing agent is destroyed by adding acetone. The insoluble salts are filtered and the filtrate is evaporated to dryness. The residue as obtained is treated with a mixture of water and dichloromethane. The organic phase is decanted, dried over dry sodium sulphate and evaporated to dryness. The residue is purified by filtration on a silica bed (elutrient: ethyl acetate). 10.78 g (0.035 mol) of the product as thus obtained are then added in small quantities to 150 ml of 12N-hydrochloric acid, previously cooled to 0° C., and left overnight at ambient temperature. The reaction medium is poured into iced water and extracted with dichloromethane. The organic phase is dried over dry sodium sulphate and evaporated to dryness. In this way, there is obtained the 2-benzoyl-1,3,4,6,7,11b-hexahydro-2H-pyrazino-[2,1-a]-4-isoquinoleinone, m.p.=160°–162° C.; total yield: 58%.

EXAMPLE 5

15 g (0.050 mol) of 4-(4-bromobenzoyl)-2,6-dioxo piperazine were dissolved in 300 ml of dimethylformamide under an inert atmosphere. 3.25 g (0.060 mol) of sodium methylate were added and the mixture was allowed to stand for 1 hour 30 minutes at ambient temperature. A solution of 21 g (0.090 mol) of 2-iodo ethyl benzene in 50 ml of dimethylformamide was added to the reaction medium, drop by drop, and the reaction medium was raised to 120° C. over 8 hours.

The reaction medium was then chilled by pouring into 3000 ml of iced water and extracted three times with ethyl acetate. The organic phases were combined and washed with water to remove residual dimethylformamide, dried over anhydrous sodium sulphate and evaporated to dryness. The oily residue obtained was crystallised from isopropyl ether, filtered and dried to obtain 4-(4-bromobenzoyl)-2,6-dioxo-1-phenethylpiperazine which existed in the form of grey crystals of melting point 110°–112° C.

14 g (0.035 mol) of the product thus obtained were dissolved under an inert atmosphere in 500 ml of ethanol and the solution was cooled to 0° C. Then, 6.5 g (0.038 ml) of cupric chloride dihydrate were added and the reaction mixture obtained was maintained at 0° C. for one hour. 6.6 g (0.175 mol) of $NaBH_4$ were added in small portions while keeping the temperature below 5° C. and the mixture was allowed to stand for 45 minutes at 0° C. The excess reducing agent was then destroyed by addition of acetone, the insoluble salts were filtered off and then the filtrate was evaporated to dryness.

The oily residue obtained was treated with a mixture of dichloromethane and water. The organic phase was decanted off, dried over anhydrous sodium sulphate and evaporated to dryness.

The residue was purified by filtration on a silica bed (ethylacetate eluant) and evaporated to dryness. The 4-(4-bromobenzoyl)-2-hydroxy-6-oxo-1-phenethylpiperazine crystallised from isopropyl ether in the form of white crystals of melting point 136°–8° C.

9.9 g (0.024 mol) of the product thus obtained were added in small quantities to 150 ml of 12N hydrochloric acid cooled to 0° C. and left to stand overnight at ambient temperature.

The reaction mixture was poured into iced water and extracted with methylene chloride. The organic phase was dried over anhydrous sodium sulphate and evaporated to dryness. The oily residue which crystallised slowly was recrystallised from a mixture of hexane/acetone to give 6.6 g of 2-(4-bromobenzoyl)-4-oxo-1,2,3,6,7,11b-hexahydro-4H-pyrazino-[2,1-a]-isoquinoline melting at 204°–206° C. (Köfler) representing a yield with respect to the 4-(4-bromobenzoyl)-2,6-dioxopiperazine of 35%.

The U.S. patents equivalent to the following German patents referred to in this application are as follows:
German Pat. No. 1,795,728: U.S. Pat. No. 3,393,195
German Pat. No. 2,362,539: U.S. Pat. No. 4,001,411
German Pat. No. 2,441,261: U.S. Pat. No. 4,051,243

The new compounds of formula XII and XIII disclosed are useful as intermediates as disclosed herein and in other chemical reactions and syntheses.

We claim:

1. A compound of formula

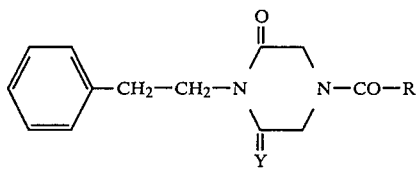

in which Y represents O or H, OH and R represents a lower alkyl group, cycloalkyl having 3 to 8 carbon atoms, phenyl or phenyl which is mono- or disubstituted with a member selected from the group consisting of halogen, hydroxy, monoloweralkyl amino, diloweralkyl amino, mercapto, thioalkyl, cyano, trifluoromethoxy, and trifluoromethylthio.

2. The compound of claim 1 which is 4-acetyl-2,6-dioxo-1-phenethyl piperazine.

3. The compound of claim 1 which is 4-benzoyl-2,6-dioxo-1-phenethyl piperazine.

4. The compound of claim 1 which is 4-(cyclohexylcarbonyl)-2,6-dioxo-1-phenethyl piperazine.

5. The compound of claim 1 which is 4-(cyclohexylcarbonyl)-2-hydroxy-6-oxo-1-phenethyl piperazine.

6. The compound of claim 1 which is 4-(4-bromobenzoyl)-2,6-dioxo-1-phenethyl piperazine.

* * * * *